US008617149B2

(12) United States Patent
Lafontaine et al.

(10) Patent No.: US 8,617,149 B2
(45) Date of Patent: Dec. 31, 2013

(54) COMMON BOND, DOUBLE-BALLOON CATHETER

(75) Inventors: Daniel M. Lafontaine, Plymouth, MN (US); Gary L. Hendrickson, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1648 days.

(21) Appl. No.: 11/541,735

(22) Filed: Oct. 2, 2006

(65) Prior Publication Data

US 2008/0171974 A1 Jul. 17, 2008

(51) Int. Cl.
*A61B 18/18* (2006.01)
*A61M 29/00* (2006.01)

(52) U.S. Cl.
USPC .................... 606/21; 604/101.01; 604/101.02

(58) Field of Classification Search
USPC .................... 606/20–22, 25; 604/101.02, 919
See application file for complete search history.

(56) References Cited

U.S. PATENT DOCUMENTS

| 3,173,418 | A |   | 3/1965  | Baran           |        |
|-----------|---|---|---------|-----------------|--------|
| 4,763,654 | A | * | 8/1988  | Jang ............................ | 606/195 |
| 5,447,497 | A |   | 9/1995  | Sogard et al.   |        |
| 5,569,184 | A |   | 10/1996 | Crocker         |        |
| 5,797,877 | A |   | 8/1998  | Hamilton et al. |        |
| 5,913,813 | A |   | 6/1999  | Williams et al. |        |
| 6,132,824 | A |   | 10/2000 | Hamlin          |        |
| 6,136,258 | A |   | 10/2000 | Wang et al.     |        |
| 6,254,570 | B1 |  | 7/2001  | Rutner          |        |
| 6,648,878 | B2 |  | 11/2003 | Lafontaine      |        |
| 2002/0156469 | A1 | * | 10/2002 | Yon et al. ........................ | 606/21 |
| 2004/0049176 | A1 |   | 3/2004  | Lafontaine      |        |
| 2005/0228368 | A1 |   | 10/2005 | Yon             |        |

FOREIGN PATENT DOCUMENTS

| WO | WO 98/09670   |   | 3/1998 |          |
|----|---------------|---|--------|----------|
| WO | WO 00/47118   |   | 8/2000 |          |
| WO | WO 2006/055941 | * | 5/2006 | A61M 29/00 |

OTHER PUBLICATIONS

PCT International Search Report and Written Opinion from corresponding PCT Application PCT/US2007/080167, mailed Feb. 26, 2008 (14 pages).

\* cited by examiner

*Primary Examiner* — Linda Dvorak
*Assistant Examiner* — Jaymi Della
(74) *Attorney, Agent, or Firm* — Seager, Tufte & Wickhem, LLC

(57) ABSTRACT

A method of manufacturing a catheter can include assembling an inner balloon within a separate outer balloon. The inner and outer balloons can each be open on opposing longitudinal ends and have a central radially expandable portion, and proximal and distal reduced diameter portions on opposite longitudinal end portions of the balloon. The method can further include bonding a portion of an inner surface of the outer balloon proximal reduced diameter portion to a portion of an outer surface of the inner balloon proximal reduced diameter portion and bonding a distal end portion of an elongate catheter shaft to a proximal portion of the bonded inner and outer balloons.

12 Claims, 8 Drawing Sheets

COMMON BOND, DOUBLE-BALLOON CATHETER

TECHNICAL FIELD

A catheter with a common-bond, double-balloon is generally described.

BACKGROUND

A number of serious medical conditions may be treated in a minimally invasive manner with various kinds of catheters designed to reach treatment sites internal to a patient's body. One such medical condition is atrial fibrillation-a serious medical condition that results from abnormal electrical activity within the heart. This abnormal electrical activity may originate from various focal centers of the heart and generally decreases the efficiency with which the heart pumps blood. It is believed that some of these focal centers reside in the pulmonary veins of the left atrium. It is further believed that atrial fibrillation can be reduced or controlled by structurally altering or ablating the tissue at or near the focal centers of the abnormal electrical activity.

Cryotherapy, or the cooling of body tissue, is one method of ablating tissue of the heart and pulmonary veins to control atrial fibrillation. Cryotherapy may be delivered to appropriate treatment sites inside a patient's heart and circulatory system by a cryotherapy catheter. A cryotherapy catheter generally includes a treatment member at its distal end, such as an expandable balloon having a cooling chamber inside. A cryotherapy agent may be provided by a source external to the patient at the proximal end of the cryotherapy catheter and delivered distally through a lumen in an elongate member to the cooling chamber where it is released. Release of the cryotherapy agent into the chamber cools the chamber, and hence the balloon's outer surface that is put in contact with tissue to perform ablation. The cryotherapy agent may be exhausted proximally through an exhaust lumen in the elongate member to a reservoir external to the patient.

SUMMARY

In some implementations, a method of manufacturing a catheter includes assembling an inner balloon within a separate outer balloon. The inner and outer balloons can each be open on opposing longitudinal ends and have a central radially expandable portion, and proximal and distal reduced diameter portions on opposite longitudinal end portions of the balloon. The method can further include bonding a portion of an inner surface of the outer balloon proximal reduced diameter portion to a portion of an outer surface of the inner balloon proximal reduced diameter portion and bonding a distal end portion of an elongate catheter shaft to a proximal portion of the bonded inner and outer balloons.

In some implementations, the catheter is a catheter for providing cryotherapy. The method can further include placing an elongate lumen structure between the inner surface and the outer surface; bonding of the inner and outer surfaces can be performed with the elongate lumen structure between the inner surface and the outer surface. Bonding of the distal end portion to the bonded inner and outer balloon can include bonding an inner surface of the outer balloon proximal reduced diameter portion to a portion of an outer surface of a distal portion of the elongate catheter shaft. The elongate catheter shaft can include a tubular structure. The method can further include introducing an assembly comprising an elongate guidewire lumen structure and a cryotherapy fluid delivery apparatus into an inner chamber of the elongate catheter shaft and inner balloon, and bonding the assembly to at least one of the elongate catheter shaft or the inner or outer balloon.

Bonding of the inner surface portion to the outer surface portion can be performed with a rigid elongate cylindrical structure positioned to extend through a passageway within the inner balloon proximal reduced portion so that the passageway does not collapse during the bonding; in some implementations, the rigid elongate cylindrical structure is a mandrel. Bonding can include exerting pressure on an outer surface of the outer balloon proximal reduced diameter portion.

In some implementations, a catheter includes a balloon assembly having an inner balloon within a separate outer balloon, the inner and outer balloons each having a central radially expandable portion, and proximal and distal reduced diameter portions on opposite longitudinal end portions of the balloon; wherein a portion of an inner surface of the outer balloon proximal reduced diameter portion is bonded to a portion of an outer surface of the inner balloon proximal reduced diameter portion; and an elongate catheter shaft having a distal end portion bonded to a proximal portion of the balloon assembly. A portion of the inner surface of the outer balloon distal reduced diameter portion can be bonded to a portion of the outer surface of the inner balloon distal reduced diameter portion.

The catheter can further include a cryo fluid delivery apparatus disposed inside the inner balloon. The catheter can further include a guidewire lumen. The catheter can further include an exhaust lumen extending through the elongate catheter shaft and in fluid communication with an inner chamber of the balloon assembly. In some implementations, the exhaust lumen is in fluid communication with a chamber between the inner and outer balloons. The catheter can further include a guidewire lumen that extends through the inner balloon.

In some implementations, a method of manufacturing a cryotherapy catheter includes assembling an inner balloon into a separate outer balloon. The inner and outer balloons can each be open on opposing longitudinal ends, and have a central radially expandable portion, and proximal and distal reduced diameter portions on opposite longitudinal end portions of the balloon. The method can further include bonding an inner surface of the outer balloon, at at least one of the proximal reduced diameter portion or distal reduced diameter portion, to an outer surface of a corresponding proximal reduced diameter portion or distal reduced diameter portion of the inner balloon; bonding a distal end portion of an elongate catheter shaft to a proximal portion of the bonded inner and outer balloons; and introducing an assembly comprising an elongate guidewire lumen structure and a cryotherapy fluid delivery apparatus into the elongate catheter shaft and inner balloon.

Bonding the inner surface of the outer balloon to the outer surface of the inner balloon can include laser bonding the inner surface to the outer surface. The method can further include adding a plug to the distal reduced diameter portion of the inner balloon to seal off the distal reduced diameter portion and to bond the distal reduced diameter portion to the assembly. The method can further include placing an elongate lumen structure between the inner surface and the outer surface, and wherein the bonding of the inner and outer surfaces is performed with the elongate lumen structure between the inner surface and the outer surface.

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
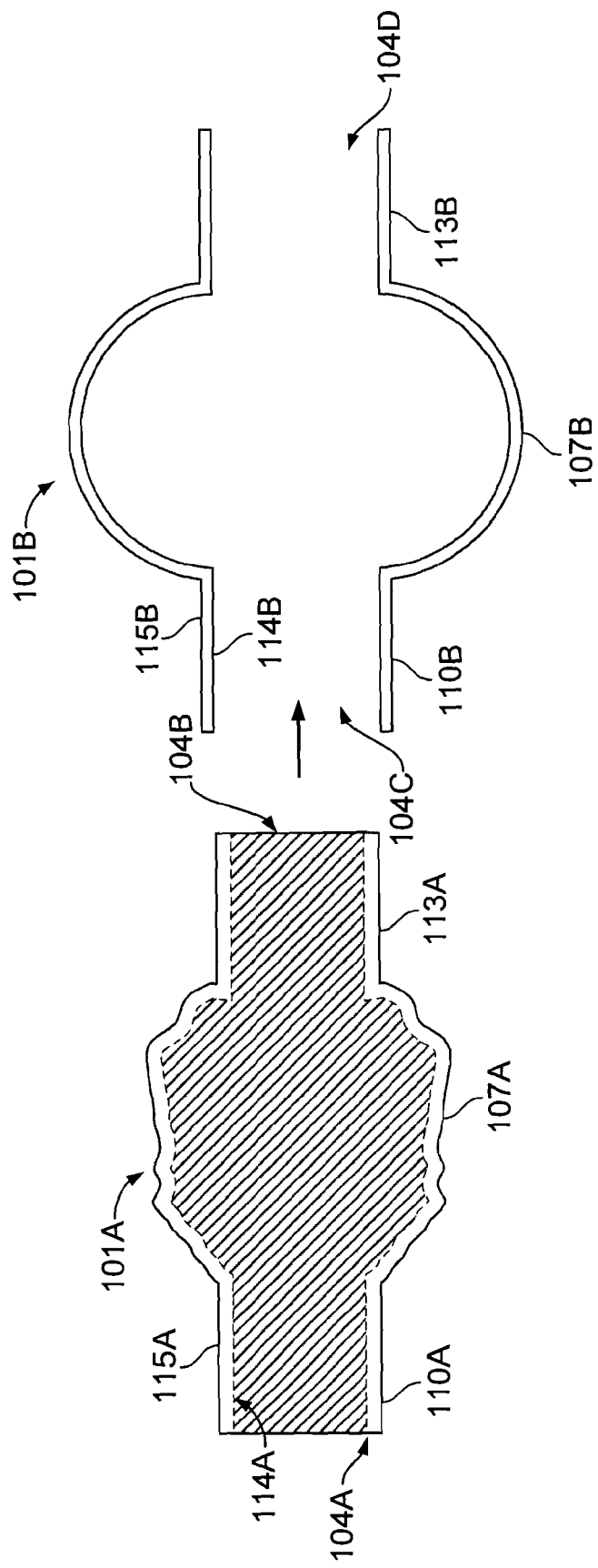
FIG. 1 illustrates inner and outer balloons that may be combined to produce a double-balloon assembly.

FIG. 1 illustrates one portion of an example process for manufacturing a double-balloon catheter. The process begins with two balloons-an inner balloon 101A and a separate outer balloon 101B. A longitudinal cross-section of the two balloons 101A and 101B is provided in FIG. 1. Each balloon 101A and 101B has opposite, open longitudinal ends 104A-D and a central radially expandable portion 107A and 107B. Each balloon also has a proximal reduced diameter portion 110A and 110B (e.g., neck portion), a distal reduced diameter portion 113A and 113B, and an inner surface 114A and 114B and outer surface 115A and 115B.

Figure 2:
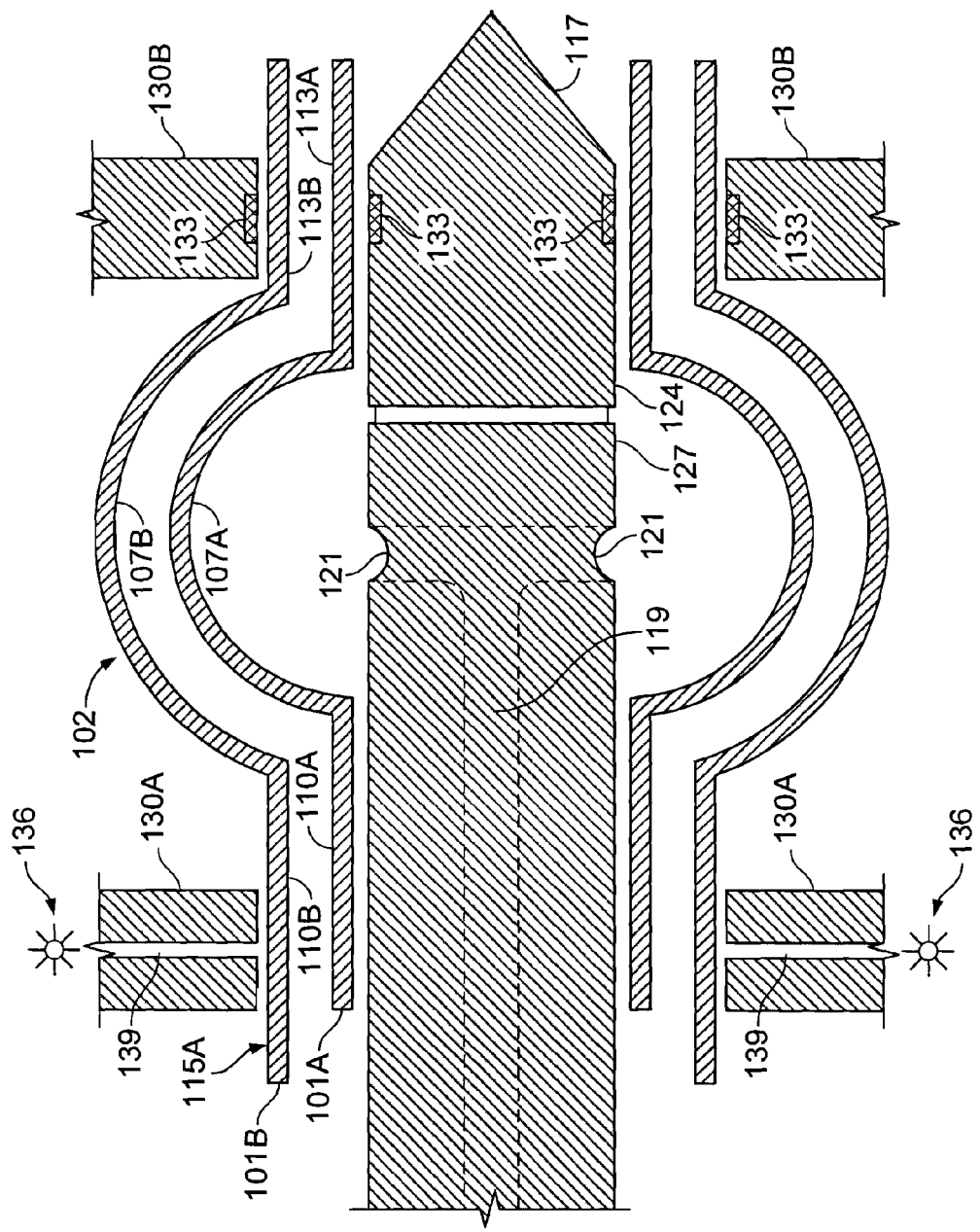
FIG. 2 illustrates a balloon assembly that may result from combination of the two balloons that are shown in FIG. 1.

As depicted by the arrow in FIG. 1, the inner balloon 101A is inserted within the outer balloon 101B to form a balloon assembly 102 that is further illustrated in FIG. 2. In some implementations, the inner balloon 101A is at least partially deflated or radially compressed and the outer balloon 101B is at least partially inflated or radially expanded. The outer balloon 101B may be secured by its proximal reduced diameter portion 101B and/or the distal reduced diameter portion 113B to manufacturing equipment (not shown). The inner balloon 101A may be temporarily secured to other manufacturing equipment, such as a mandrel 117 (shown in FIG. 2) to facilitate insertion into the outer balloon 101B. In some implementations, the inner balloon 101A is radially compressed by being twisted. For example, the distal reduced diameter portion 113A can be twisted relative to the proximal reduced diameter portion 110A by the manufacturing equipment. In other implementations, a rigid guide such as the mandrel 117 can seal against the proximal reduced diameter 110A and the distal reduced diameter portion 113A, and the mandrel 117 can provide a pressure source (depicted in FIG. 2) that radially compresses the central radially expandable portion 107A of the inner balloon 101A.

FIG. 2 illustrates an example balloon assembly 102 formed by inserting the inner balloon 101A into the outer balloon 101B. As shown, the central radially expandable portion 107A of the inner balloon 101A is at least partially re-expanded, although re-expansion is not required. To re-expand the inner balloon 101A, the example mandrel 117 can include a pressure source that either draws a vacuum to compress the central radially expandable portion 107A, or exerts pressure to expand the radially expandable portion 107A. The pressure source can be coupled to the interior of the inner balloon via a mandrel lumen 119 and mandrel orifices 121. Alternatively, the mandrel 117 can have a distal tip portion 124 that rotates relative to a body portion 127, and the distal tip portion 124 can be rotated to either twist and radially compress the inner balloon or untwist and radially expand the inner balloon 101A.

Once the inner balloon 101A is disposed inside the outer balloon 1013B, the balloons 101A and 1101B are bonded together to form the balloon assembly 102. In some implementations, either or both of the proximal reduced diameter portions 110A and 110B or the distal reduced diameter portions 113A or 113B are bonded together by applying pressure to the outer surface 115A of the outer balloon 1101B (e.g., with clamps 130A or 130B), such that a reduced diameter portion 110B or 113B of the outer balloon 101B is brought into contact with a corresponding reduced diameter portion 110A or 113A of the inner balloon 101A. After the two balloons 101A and 101B are in contact, they can be bonded with an adhesive or through application of thermal energy. In some implementations, thermal energy is applied directly, for example, by heating elements 133 in the mandrel 117 and/or clamps 130B. In some implementations, thermal energy is applied by a laser source 136, for example, through channel 139 in the clamp 130A to laser bond the inner balloon 101A and the outer balloon 101B together.

Figure 3:
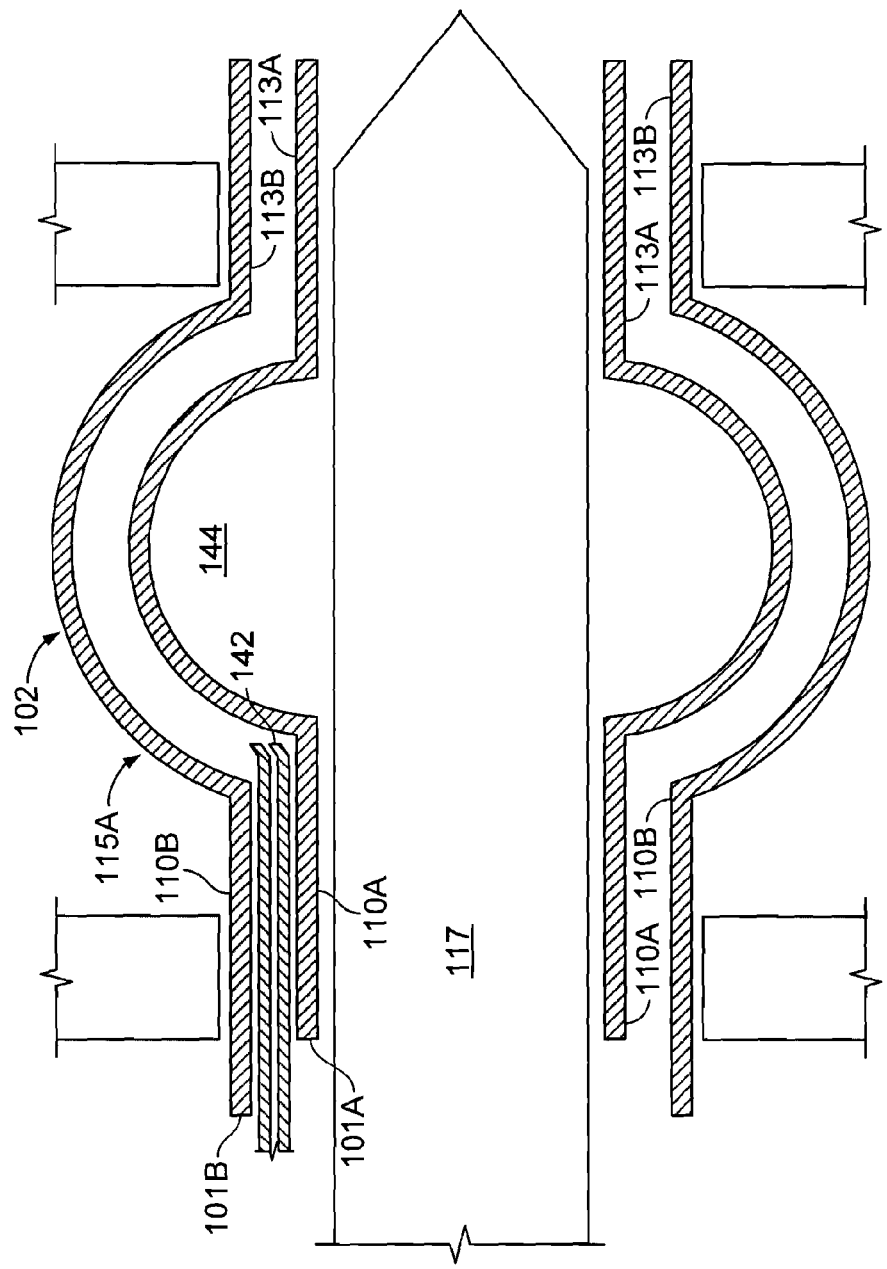
FIG. 3 illustrates another balloon assembly that may result from the combination of the two balloons that are shown in FIG. 1.

In some implementations, as shown in FIG. 3, a vacuum lumen 142 is disposed between the inner balloon 101A and the outer balloon 101B, and the balloons 101A and 101B are subsequently bonded together around the vacuum lumen 142. During operation of a corresponding balloon catheter, the vacuum lumen 142 can provide a way to evacuate any liquids or gases that escape from a chamber 144 defined by the inner balloon 101A. For example, in the case of a cryotherapy catheter, the vacuum lumen 142 can be used to evacuate cryotherapy fluid from the balloon assembly in the case of a rupture of the inner balloon 101A. The vacuum lumen 142 can also facilitate control of the space between the inner balloon 101A and the outer balloon 101B. For example, a vacuum source can be applied to the vacuum lumen 142 in order to draw the outer balloon 101B against the inner balloon 101A, or a pressure source may be applied to force the outer balloon 101B away from the inner balloon 101A. In the case of a cryotherapy catheter, regulating spacing between the inner balloon 101A and the outer balloon 101B can have the effect of indirectly controlling temperature of the outer surface 115A of the outer balloon 101B.

In some implementations, the inner balloon 101A and outer balloon 101B are bonded together and around the vacuum lumen 142 in a manner similar to that described with reference to FIG. 2. That is, a reduced diameter portion 110B of the outer balloon 101B is brought into contact with a corresponding reduced diameter portion 110A of the inner balloon 101A and with the exterior of the vacuum lumen 142. The inner balloon 101A and outer balloon 101B are then bonded together (e.g., with adhesive or thermal or laser bonds). As a result of the bonding process, the inner balloon 101A and outer balloon 101B can be completely bonded together and sealed about the circumference of the corresponding reduced diameter portions 110 and 110B (or 113A and 113B).

Figure 4A:
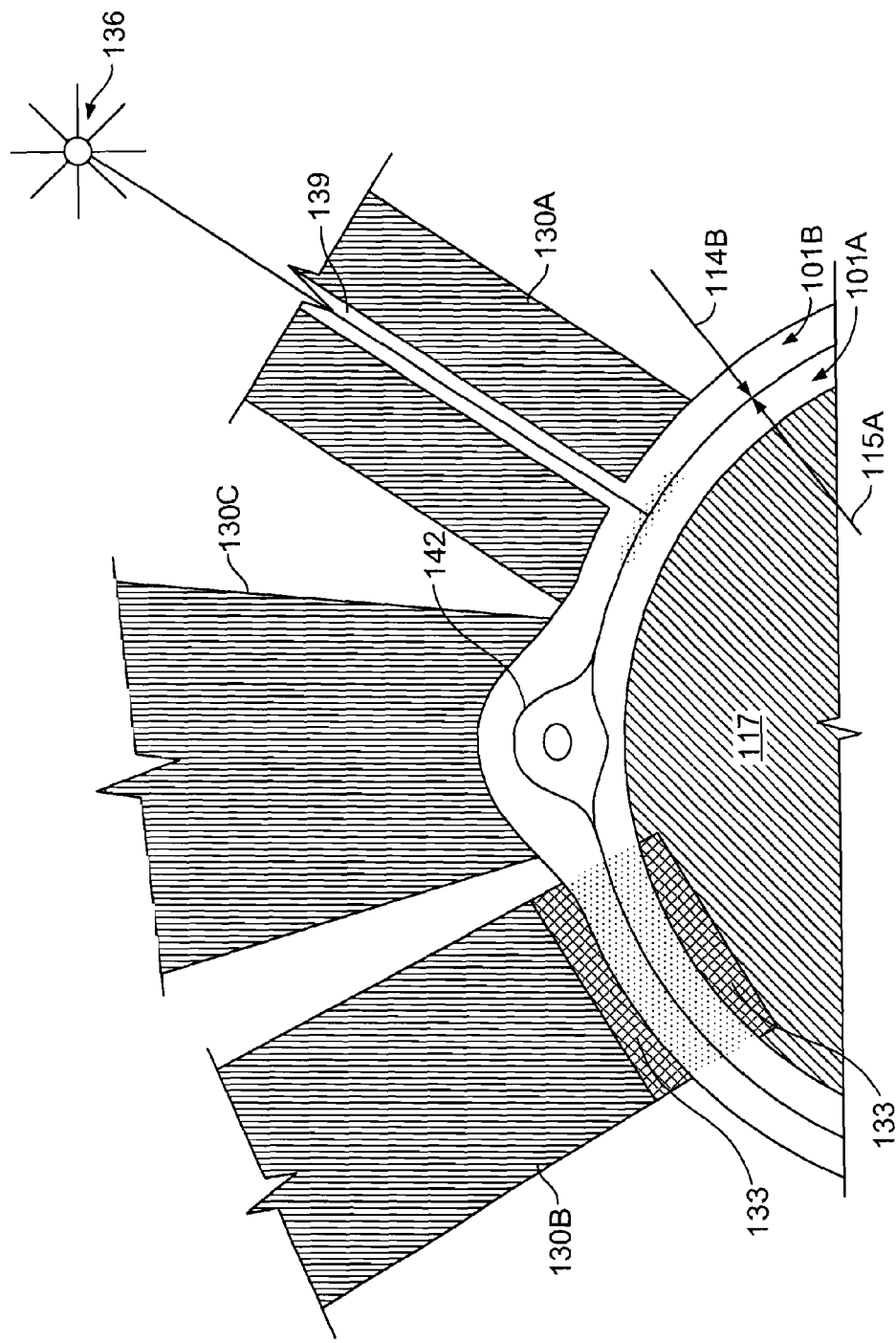
FIG. 4A is a cross-sectional view showing details of an exemplary bond between the inner and outer balloons.

FIG. 4A is a cross-section showing additional details of an exemplary bond between a reduced diameter portion of the inner balloon ("inner balloon 101A") and a corresponding reduced diameter portion of the outer balloon ("outer balloon 101B"). As shown in FIG. 4A, a vacuum lumen 142 is included between the inner balloon 101A and outer balloon 101B; in other implementations, the vacuum lumen is omitted.

Two methods of bonding are depicted in FIG. 4A. According to a first method, heating elements 133 in the mandrel 117 and/or a corresponding clamp portion 130B provide thermal energy that softens or melts the material of the inner balloon 101A and outer balloon 101B such that the balloons 101A and 101B bond. According to a second 1o method, a laser source 136 provides thermal energy to the inner balloon 101A and outer balloon 101B such that the balloons 101A and 101B are bonded together. In particular, the laser energy can be delivered via channel 139 in the clamp 130A. In some implementations, materials of the inner balloon 101A and the outer balloon 101B are selected such that the outer balloon 101B allows much of the laser energy to pass through, while the inner balloon 101A absorbs substantially all of the laser energy, thereby generating heat at the inner surface 114 of the outer balloon 101B and the outer surface 115A of the inner balloon 101A such that the balloons 101A and 101B bond.

In some implementations, the clamps 130A, 130B or 130C are segmented, as shown, to facilitate radially expansion or compression capable of applying pressure to the outer balloon 101B around substantially all of the circumference. In some implementations, other techniques are used to bring the outer balloon 101B into contact with the inner balloon 101A. For example, some implementations can employ a vacuum source or pressure source to bring the balloons 101A and 101B into contact.

Figure 4B:
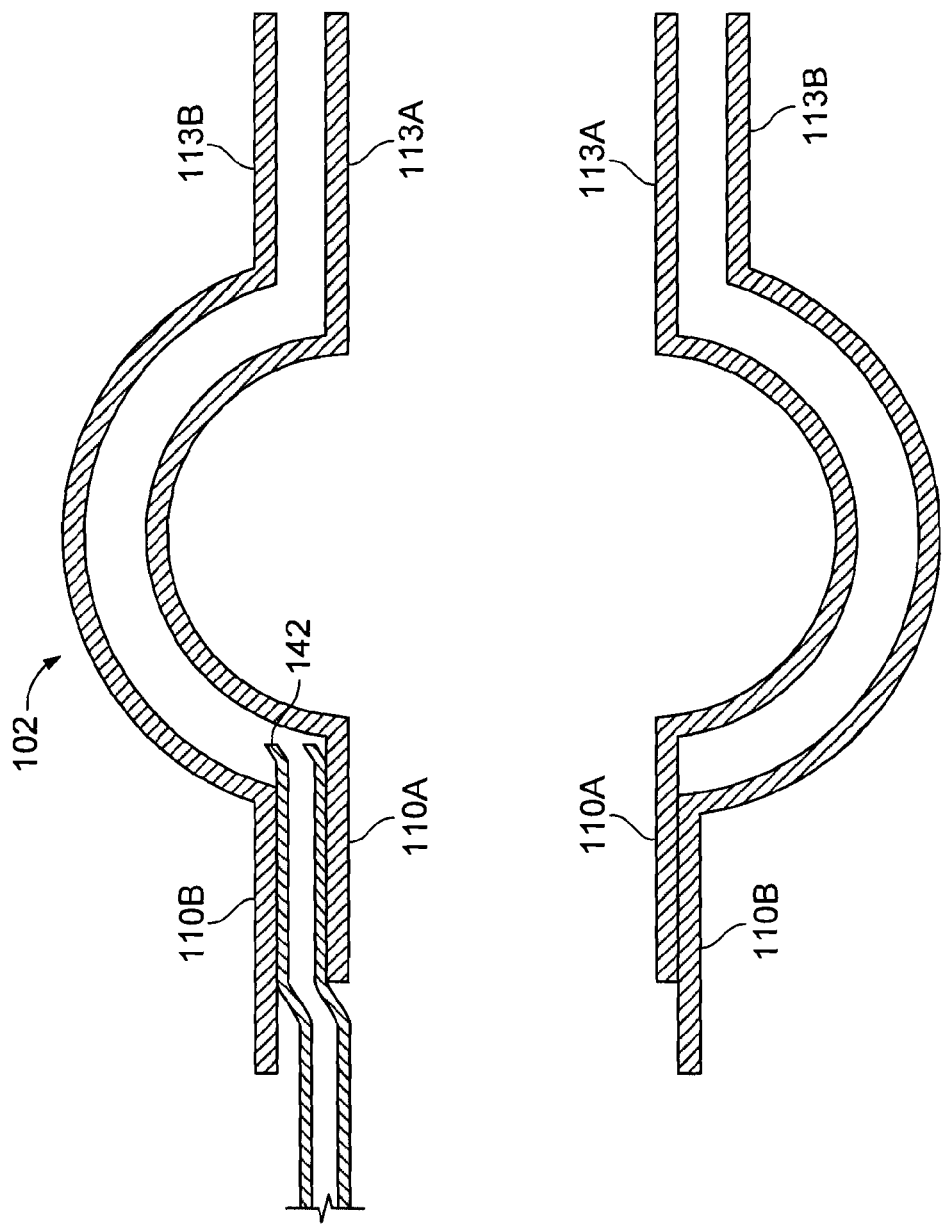
FIG. 4B is a longitudinal cross-section showing additional details of an exemplary bond between the inner and outer balloons.

FIG. 4B illustrates a longitudinal cross-section of the balloon assembly 102. As shown, the proximal reduced diameter portions 110A and 110B are bonded together, and the distal reduced diameter portions 113A and 113B are not bonded together. In some implementations, both reduced diameter portions 110A and 110B and 113A and 113B are bonded together. In other implementations, only the distal reduced diameter portions 113A and 113B are bonded together (at this stage in the manufacturing process).

Figure 5:
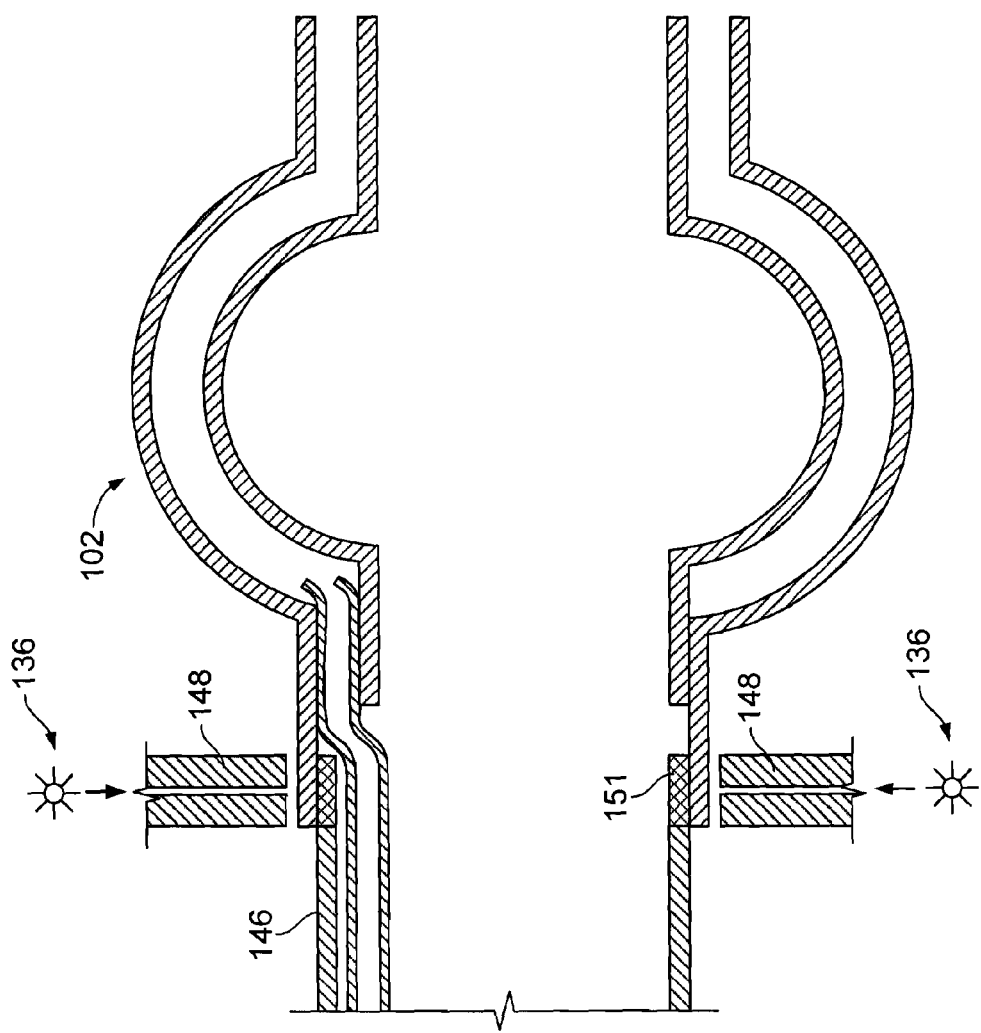
FIG. 5 illustrates a balloon assembly bonded to an elongate shaft of a catheter.

After the balloon assembly 102 is formed by bonding the inner balloon 101A to the outer balloon 101B at one or both of the corresponding proximal reduced diameter portions 110A and 110B or distal reduced diameter portions 113A and 113B, the balloon assembly 102 is bonded to an elongate catheter shaft 146, as shown in FIG. 5. In some implementations, the balloon assembly 102 is bonded to the elongate catheter shaft 146 in a similar manner as the balloons 101A and 101B are bonded together. For example, the s balloon assembly 102 can be secured against the elongate catheter shaft 146 via clamps 148, and once secured, a laser source 136 can be employed to laser bond the balloon assembly 102 to the elongate catheter shaft 146. As another example, the balloon assembly 102 can be secured to the elongate catheter shaft 146 with adhesive or by direct thermal bonding (e.g., with heat provided by a heating element).

In some implementations, a mandrel (not shown in FIG. 5) is inserted into the balloon assembly 102 to facilitate bonding between the balloon assembly 102 and elongate catheter shaft 146. In some implementations, the elongate catheter shaft 146 includes a stiff region 151 that resists compression by the clamps to facilitate bonding without a mandrel.

Figure 6:
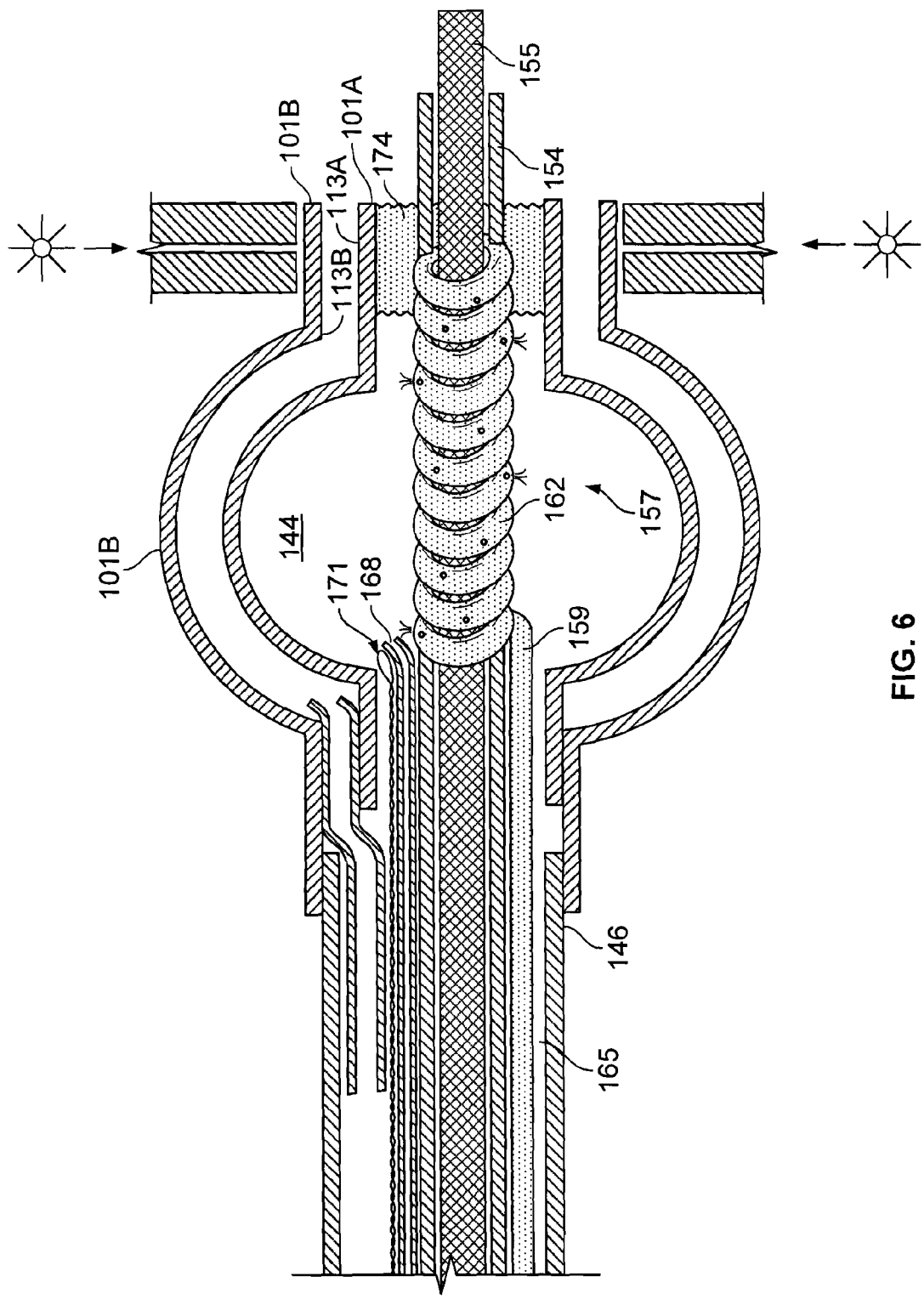
FIG. 6 illustrates additional components of an exemplary catheter.

As shown in FIG. 6, other catheter components can be inserted into the balloon assembly 102. For example, a guidewire lumen 154 can be added. In some implementations, to facilitate assembly, the guidewire lumen 154 includes a stiffening wire 155 that is removed after assembly. Steerable catheters that are not "over-the-wire" may omit the guidewire lumen 154.

A cryotherapy fluid delivery apparatus 157 (shown in three dimensions rather than as a longitudinal cross section) can also be added. In operation, cryo fluid can be delivered from a source external to the catheter (shown in FIG. 7) via cryotherapy fluid delivery lumen 159 to a cooling chamber 144 inside the inner balloon 101A, where it is released to cool tissue that is adjacent to the outer balloon 101B. In some implementations, the cryo fluid is released from a coiled portion of the cryotherapy fluid deliver lumen 159 via orifices 162 where the cryo fluid undergoes a phase change, to a gas, within the cooling chamber 144 (the so-called Joule-Thomson effect). The gas can then be exhausted though an exhaust lumen 165, which, in some implementations, is simply the internal lumen formed by the body of the elongate catheter shaft 146.

Other components can be added to the catheter as well. For example, as shown, the catheter includes a pressure-sensing lumen 168 by which pressure inside the cooling chamber 144 can be sensed by devices external to the catheter. A thermocouple 171 or other temperature-sensing device can also be added to the catheter. In some implementations, the thermocouple 171 is integrated in the pressure-sensing lumen 168. In some implementations, the cryo fluid delivery apparatus 157 and guidewire lumen 154 may be preassembled and added to the catheter as a single assembly.

Once all of the components have been added to the catheter, the end of the catheter is sealed, and the distal reduced diameter portion 113B of the outer balloon 101B is bonded to the distal reduced diameter portion 113A of the inner balloon 101A, if this has not already been done. As depicted in FIG. 6, the distal regions of the inner balloon 101A and outer balloon 101B are laser bonded together. In some implementations, the distal portions of the outer balloon 101B and inner balloon 101A are laser bonded to the cryotherapy fluid deliver apparatus 157 and/or the guidewire lumen 154. In other implementations, an adhesive "plug" 174 is used to bond the inner balloon 101A to the guidewire lumen 154 and cryotherapy fluid deliver apparatus 157 and to seal off the distal portion of the cooling chamber 144.

Figure 7:
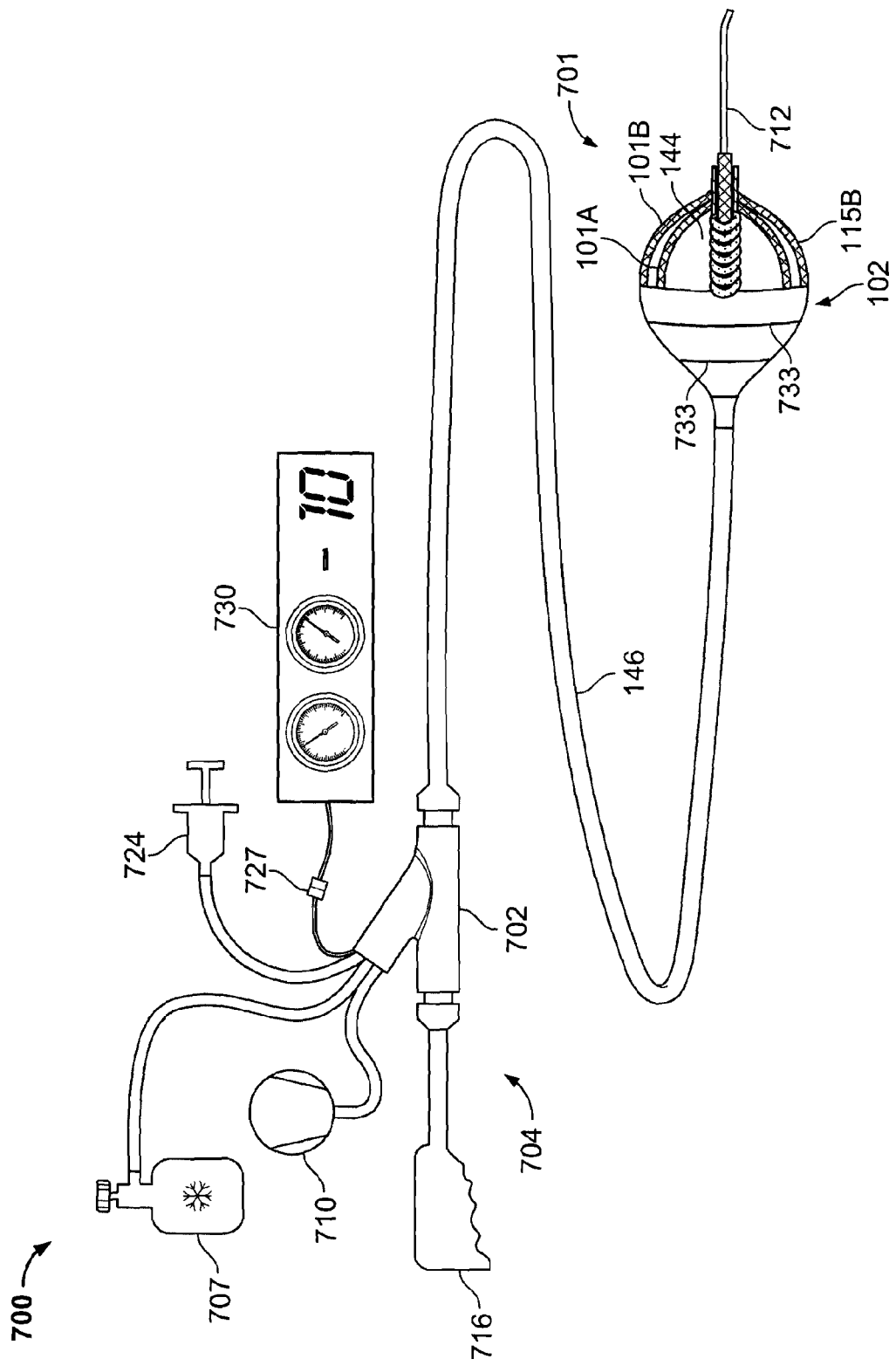
FIG. 7 illustrates an exemplary double-balloon catheter device.

An example cryotherapy catheter 700, shown in FIG. 7, includes the elongate member 146 with the inflatable balloon assembly 102 at a distal end 701. In some implementations, as described above, the balloon assembly 102 has an internal chamber 144 to which cryotherapy fluid is delivered to cool the internal chamber 144, the external surface 11 5B of the balloon assembly 102, and adjacent body tissue. A port device 702 is attached to a proximal end 704 of the elongate member 146. The port device 702 provides connections to various external equipment, including a cryotherapy fluid source 707 and an exhaust reservoir 710.

The catheter's elongate member 146 has multiple internal lumens (not shown in FIG. 7). The internal lumens allow cryotherapy fluid to be delivered distally from the external cryotherapy fluid source 707 to the internal chamber 144 of the balloon assembly 102. In addition, the internal lumens of the elongate member 146 allow exhaust resulting from delivery of cryotherapy fluid to the internal chamber 144 to be delivered proximally from the internal chamber 144 to the external exhaust reservoir 720. During operation, there can be continuous circulation within the elongate member 146 of cryotherapy fluid distally and exhaust proximally.

The example catheter 700 shown in FIG. 7 is an over-the-wire type catheter. Such a catheter employs a guidewire 712 (and corresponding guidewire lumen 154, not shown in FIG.

7), which is shown as extending from the distal end 701 of the catheter 700. In some implementations, the guidewire 712 can be pre-positioned inside a patient's body; once the guidewire 712 is properly positioned, the balloon assembly 102 (in a deflated state) and the elongate member 146 can be routed over the guidewire 712 to a treatment site. In some implementations, the guidewire 712 and balloon assembly 102 portion of the catheter 700 can be advanced together to a treatment site inside a patient's body, with the guidewire portion 712 leading the balloon assembly 102 by some distance (e.g., several inches). When the guidewire portion 712 reaches the treatment site, the balloon can then be advanced over the guidewire 712 until it also reaches the treatment site.

The catheter 700 includes a manipulator 716, by which a medical practitioner can navigate the guidewire 712 and balloon assembly 102 through a patient's body to a treatment site. In some implementations, release of cryotherapy fluid into the cooling chamber 144 inflates the balloon assembly 102 to a shape similar to that shown in FIG. 7. In other implementations, a pressure source 724 can be used to inflate the balloon assembly 102 independently of the release of cryotherapy fluid into the internal chamber 144 of the balloon assembly 102. The pressure source 724 can also be used to inflate an anchor member on the end of the guidewire 712 (not shown). The catheter 700 includes a connector 727 for connecting monitoring equipment 730. The monitoring equipment 730 can be used, for example, to monitor temperature or pressure at the distal end 701 of the catheter 700. To aid in positioning the balloon assembly 102 of the catheter 700 inside a patient's body, various marker bands 733 are also disposed at the distal end 701 of the catheter 700. The marker bands 733 may be opaque when the catheter 700 is viewed by x-ray or other imaging techniques.

In some implementations, the balloons 101A and 101B in the balloon assembly 102 are formed from a polymer including, but not limited to, polyolefin copolymer, polyester, polyethylene teraphthalate, polyethylene, polyether-block-amide, polyamide, polyimide, nylon, latex, or urethane. For example, certain implementations of the balloon assembly 102 include PEBAX® 7033 material (70D poly ether amide block). The individual balloons 101A and 101B in the balloon assembly 102 can be made by blow-molding a polymer extrusion into the desired shape. In some implementations, one or both of the balloons 101A or 101B can be constructed to expand to a desired shape when pressurized without elastically deforming substantially beyond the desired shape.

A number of ancillary processes can be used to affect the material properties of the balloons 101A or 101B. For example, the polymer extrusion can be exposed to gamma radiation which may alter the polymer infrastructure to provide uniform expansion during blow molding and additional burst strength when in use. In addition, a balloon 101A or 101B can be exposed to a low temperature plasma field which may alter the surface properties to provide enhanced adhesion characteristics. Those skilled in the art will recognize that other materials and manufacturing processes may be used to provide a balloon assembly 102 suitable for use with the catheter.

A number of implementations have been described. Nevertheless, it will be understood that various modifications may be made without departing from the spirit and scope of the disclosed implementations. Accordingly, other implementations are within the scope of the following claims.

What is claimed is:

1. A method of manufacturing a catheter, the method comprising:

assembling an inner balloon within a separate outer balloon, the inner and outer balloons each being open on opposing longitudinal ends, having a central radially expandable portion, and proximal and distal reduced diameter portions on each opposing longitudinal end;

placing an elongate lumen structure between an inner surface of the outer balloon proximal reduced diameter portion and an outer surface of the inner balloon proximal portion;

bonding a portion of the inner surface of the outer balloon proximal reduced diameter portion, a portion of the outer surface of the inner balloon proximal reduced diameter portion, and an outer surface of the elongate lumen structure to fix the elongate lumen structure between the outer balloon proximal reduced diameter portion and the inner balloon proximal reduced diameter portion; and bonding a distal end portion of an elongate catheter shaft to a proximal portion of the bonded inner and outer balloons such that the elongate lumen structure extends from distal of proximal ends of the inner and outer balloons to proximal of the inner and outer balloons and into a lumen of the elongate catheter shaft;

wherein the bonding of the portion of the inner surface of the outer balloon proximal reduced diameter portion and the portion of the outer surface of the inner balloon proximal reduced diameter portion is performed with the elongate lumen structure between the portion of the inner surface of the outer balloon proximal reduced diameter portion and the portion of the outer surface of the inner balloon proximal reduced diameter portion such that the inner surface of the outer balloon proximal reduced diameter portion, the outer surface of the inner balloon proximal reduced diameter portion, and the outer surface of the elongate lumen structure are bonded to one another;

wherein after completion of the method of manufacturing the catheter, a line extending perpendicular to and passing through a central longitudinal axis of the catheter passes through, in order, a first side of a wall of the proximal reduced diameter portion of the outer balloon, a first side of a wall of the proximal reduced diameter portion of the inner balloon, a second side of the wall of the proximal reduced diameter portion of the inner balloon, a first side of a wall of the elongate lumen structure, a second side of the wall of the elongate lumen structure, and a second side of the wall of the proximal reduced diameter portion of the outer balloon.

2. The method of claim 1, wherein the catheter is a catheter for providing cryotherapy.

3. The method of claim 1, wherein the bonding of the distal end portion of the elongate catheter shaft to the proximal portion of the bonded inner and outer balloons comprises bonding the inner surface of the outer balloon proximal reduced diameter portion to a portion of an outer surface of the distal end portion of the elongate catheter shaft.

4. The method of claim 1, wherein the elongate catheter shaft comprises a tubular structure.

5. The method of claim 1, further comprising introducing an assembly comprising an elongate guidewire lumen structure and a cryotherapy fluid delivery apparatus into an inner chamber of the elongate catheter shaft and inner balloon, and bonding the assembly to at least one of the elongate catheter shaft, the inner balloon, or the outer balloon.

6. The method of claim 1, wherein the bonding of the portion of the inner surface of the outer balloon proximal reduced diameter portion and the portion of the outer surface of the inner balloon proximal reduced diameter portion is performed with a rigid elongate cylindrical structure positioned to extend through a passageway within the inner balloon proximal reduced portion so that the passageway does not collapse during the bonding.

7. The method of claim 6, wherein the rigid elongate cylindrical structure is a mandrel.

8. The method of claim 6, wherein the bonding of the portion of the inner surface of the outer balloon proximal reduced diameter portion and the portion of the outer surface of the inner balloon proximal reduced diameter portion comprises exerting pressure on an outer surface of the outer balloon proximal reduced diameter portion.

9. The method of claim 1, wherein the elongate lumen structure has a distal end with an opening therein and wherein the step of bonding of the portion of the inner surface of the outer balloon proximal reduced diameter portion and the portion of the outer surface of the inner balloon proximal reduced diameter portion is performed when the distal end of the elongate lumen structure is in the central radially expandable portion of the outer balloon.

10. The method of claim 1, wherein the elongate lumen structure has a length less than a length of the catheter shaft.

11. A method of manufacturing a catheter, the method comprising:
  assembling an inner balloon within a separate outer balloon, the inner and outer balloons each being open on opposing longitudinal ends, having a central radially expandable portion, and proximal and distal reduced diameter portions on each opposing longitudinal end;
  placing an elongate lumen structure between an inner surface of the outer balloon proximal reduced diameter portion and an outer surface of the inner balloon proximal portion;
  bonding a portion of the inner surface of the outer balloon proximal reduced diameter portion to a portion of the outer surface of the inner balloon proximal reduced diameter portion with the elongate lumen structure between the portion of the inner surface of the outer balloon proximal reduced diameter portion and the portion of the outer surface of the inner balloon proximal reduced diameter portion such that the inner surface of the outer balloon proximal reduced diameter portion, the outer surface of the inner balloon proximal reduced diameter portion, and an outer surface of the elongate lumen structure are bonded to one another, thereby fixing the elongate lumen structure between the outer balloon proximal reduced diameter portion and the inner balloon proximal reduced diameter portion;
  bonding a distal end portion of an elongate catheter shaft to a proximal portion of the bonded inner and outer balloons such that the elongate lumen structure extends from distal of proximal ends of the inner and outer balloons to proximal of the inner and outer balloons and into a lumen of the elongate catheter shaft.

12. The method of claim 11, wherein the elongate lumen structure has a length less than a length of the catheter shaft.

* * * * *